United States Patent [19]
Yarnitzky

[11] Patent Number: 6,022,470
[45] Date of Patent: Feb. 8, 2000

[54] ELECTROANALYTICAL, DROPPING MERCURY ELECTRODE CELL

[75] Inventor: Chaim Noah Yarnitzky, Haifa, Israel

[73] Assignee: VerdEco Technologies Ltd., Yoqneam, Israel

[21] Appl. No.: 08/945,766

[22] PCT Filed: Apr. 30, 1996

[86] PCT No.: PCT/EP96/01794

§ 371 Date: Mar. 13, 1998

§ 102(e) Date: Mar. 13, 1998

[87] PCT Pub. No.: WO96/35117

PCT Pub. Date: Nov. 7, 1996

[30] Foreign Application Priority Data

May 1, 1995 [IL] Israel .......................... 113564

[51] Int. Cl.[7] .............. G01F 1/64; G01N 17/00; G01N 27/26

[52] U.S. Cl. ............... 205/775; 205/789.5; 204/409; 204/412; 204/413

[58] Field of Search ................. 204/413, 409, 204/412, 434; 205/775, 789, 789.5

[56] References Cited

U.S. PATENT DOCUMENTS

| | | |
|---|---|---|
| 2,343,885 | 3/1944 | Coleman . |
| 3,210,261 | 10/1965 | Tyler .................... 204/409 |
| 3,922,205 | 11/1975 | Mc Lean et al. . |
| 4,138,322 | 2/1979 | Barnes et al. . |
| 4,259,360 | 3/1981 | Venetucci et al. ............ 426/231 |
| 4,260,467 | 4/1981 | Smith et al. . |
| 4,436,590 | 3/1984 | Miles et al. . |
| 4,496,454 | 1/1985 | Berger . |
| 4,500,411 | 2/1985 | Yarnitzky ................. 204/413 |
| 4,917,776 | 4/1990 | Taylor . |
| 5,112,357 | 5/1992 | Bjerklund et al. . |
| 5,296,123 | 3/1994 | Reddy et al. . |
| 5,578,178 | 11/1996 | Nuzzio .................... 204/413 |
| 5,597,464 | 1/1997 | Saur ......................... 204/13 |
| 5,641,686 | 6/1997 | Aldstadt, III ............. 204/434 |

FOREIGN PATENT DOCUMENTS

| | | |
|---|---|---|
| 2531224 | 2/1984 | France . |
| 1281341 | 5/1972 | United Kingdom . |

Primary Examiner—Robert J. Warden, Sr.
Assistant Examiner—Kaj K. Olsen
Attorney, Agent, or Firm—Michael N. Meller; Eugene Lieberstein

[57] ABSTRACT

The electroanalytical, voltammetric cell includes a cell body housing, in addition to a reference electrode, a working electrode and, in its lowermost portion, a counter-electrode. An arrangement for deoxygenating the sample solution includes feeding the sample solution through a deoxygenation conduit in contact with a stream of an inert gas. An inlet for the deoxygenated sample solution is provided in the cell body in the space between the working electrode and the counter-electrode, and an exit for the sample solution is provided in the cell body at a level above the working electrode. Vacuum and/or pressure is utilized for causing the sample solution to flow to the exit, to be discharged from the cell above the working electrode, thus assuring that the space between the working electrode and the counter-electrode is constantly filled with sample solution.

17 Claims, 5 Drawing Sheets

ELECTROANALYTICAL, DROPPING MERCURY ELECTRODE CELL

FIELD OF THE INVENTION

This invention relates to an improved voltammetric cell, particularly, though not exclusively, of the dropping mercury electrode (hereinafter DME) type, very suitable for industrial use, and is characterized by high reliability, ease of operation and long life.

BACKGROUND OF THE INVENTION

Electrochemical detector and voltammetric cells are known in the art and have been used with success for the analysis of flowing solution in the laboratory. Two-electrode and three-electrode cells are known. The three-electrode cell comprises a working electrode, a counter-electrode and a reference electrode which has the function of establishing and maintaining a constant potential relative to the working electrode or the sample solution. The sample solution is flown continuously through the cell. In principle, the electrodes may be affected by poisoning due to absorption with resulting passivation and loss of signaL In order to avoid such poisoning, the dropping mercury electrode has been adopted in many such cells.

U.S. Pat. No. 3,922,205 describes the basic structure of a polarographic-cell. U.S. Pat. No. 4,138,322 discloses a structure of shielded dropping mercury cathode. U.S. Pat. No. 4,260,467 describes a dropping mercury electrode which comprises a reservoir for liquid mercury, a mercury capillary at the outlet end of which mercury drops are formed, and a valve for selective air-purging passage of mercury from the reservoir to the inlet end of the capillary. An automated polarographic cell is described by C. N. Yarnitzky in Analytical Chemistry, Vol. 57, No. 9, August 1985, p. 2011–2015.

The efficiency of polarographic cells of the aforesaid type depends on the combination of a number of structural and fuctional features. A fully satisfactory combination, providing an industrially efficient such cell has not been achieved so far in the art. The cells which are automatic and also on-line are expensive and not adequately efficient. In many cases, the prior art cells use a solid electrode which becomes polluted with time, so that the cell ceases to be reliable. In on-line, in-flow cells, the signal obtained is often proportional to the Reynolds number. Because of this, attempts have been made to design small cells, having high Reynolds number, comprising means for producing and controlling the dropping of the mercury electrode. Such means, however, being complicated and unreliable. Other cells are objectionable in that they require a very large volume of the sample solution, with resulting waste of time and chemicals.

High sensitivity and short reaction time, viz. quick response, are particularly important in on-line cells and esing cells are not satisfactory in this respect. If, for instance, metal pollution occurs in an on-line system in which such a cell is inserted, a delayed reaction on the part of the cell and the consequent failure to reveal the pollution until a significant period of time has elapsed and the pollution may have reached a high level, negatively affects the operation of the system.

Among the specific problems encountered by polarographic cells employing a dropping mercury electrode of the prior art, two are particularly important. Firstly, the presence of oxygen in sample solution having a strong negative effect on the accuracy of the measurements, the oxygen must be removed as fully as possible before all the solution is fed into the polarographic cell proper. For this purpose, it has been proposed to cause the sample solution to flow in a thin layer, together with a stream of nitrogen, in a tube which leads it close to the position at which the mercury drops are formed. This arrangement, however, has been found to be unsatisfactory, and it is believed that this is due to the fact that it does not assure that the space between the counter-electrode, the reference electrode and the working electrode be always full with the sample solution, and consequently, the electrical contact between the electrodes is interrupted at times, thereby requiring interrupting the measurement and starting it anew.

Another important problem that the prior art has not satisfactorily solved, is to synchronize the measurements with the formation and the fall of the mercury drop. For the measurements to be reliable, they must be made when the drop that constitutes the working electrode has a given area. Since the area of the drop increases during its formation and until the drop is detached from the capillary from which the mercury issues, the need arises to control the separation of the drop and synchronize it with the measurements. For this purpose, it has been proposed to employ mechanical means, such as a hammer device which imparts to the mercury capillary a series of blows, to cause the detachment and fall of the mercury drop at a desired time. This system, however, is unreliable and further subjects the capillary to mechanical stresses and solution creeps in, which considerably shorten its life.

It is a purpose of this invention to provide an electroanalytical voltammetric cell, particularly, but exclusively of the dropping mercury electrode (DME) type, which is free from the drawbacks of the prior art cells.

It is another object of the invention to provide such a cell in which the electrical contact, via the sample solution, between the counter-electrode and the working electrode is constantly assured.

It is a further purpose of this invention to provide such a cell which has a very short reaction time and a very quick response.

It is a still further purpose of this invention to provide such a cell having a dropping mercury electrode, in which the measurement of the current passing through the same (which has a short, but significant duration, typically of a few seconds) is synchronized with the fall of the mercury drop, and its beginning and its end occur at predetermined, constant times of said drop, without applying mechanical stresses, such as blows, to the apparatus element where the mercury drop is formed.

It is a still further purpose of the invention to provide all of the aforesaid features and advantages with a structure that is simple, reliable, inexpensive to make and durable in operation.

It is a still further purpose of the invention to provide an electrochemical voltammetric cell having an optimal combination of structural and functional features, to permit efficient and reliable industrial use.

Other purposes and advantages of the invention will appear as the description proceeds.

SUMMARY OF THE INVENTION

The voltammetric cell according to the invention is characterized in that it comprises:
  a) a cell body housing, in addition to a reference electrode, a working electrode and, in its lowermost portion, a counter-electrode;

b) means for removing oxygen from the sample solution;

c) means for feeding the sample solution to said deoxygenation means, means for feeding a stream of an inert gas to said deoxygenation means, and means for causing said solution to flow in said deoxygenation means, whereby oxygen is removed therefrom by contact with said inert gas;

d) a means for removing said inert gas from said deoxygenation means after deoxygenation of the sample solution;

e) an inlet for the deoxigenated sample solution provided in said cell body in the space between said working electrode and said counter-electrode;

f) an exit for the sample solution provided in said cell body at a level above said working electrode; and g) vacuum and/or pressure means for causing said sample solution to flow to said exit, to be discharged from the cell above said working electrode, thus assuring that the space between said working electrode and said counter-electrode is constantly filled with said sample solution Preferably, the working electrode is chosen from among mercury, gold, platinum and glassy carbon electrodes, and more preferably is a DME, comprising a mercury capillary fed with mercury from a mercury reservoir, whereby a drop mercury electrode is periodically formed and separated from the lowermost end of said capillary.

Also, preferably, the deoxygenation means comprises a deoxygenation conduit and means for feeding thereto the sample solution and an inert gas, said conduit comprising a deoxygenation section wherein the solution and the gas flow together in equicurrent and branching out at the end of said deoxygenation section into an upwardly directed branch and a downwardly directed branch, an inlet being provided for said downwardly directed branch in said cell body in the space between said working electrode and said counter-electrode and an inlet being provided for said upwardly directed branch in said cell body above said working electrode, the sample solution flowing through said downwardly directed branch to said inlet provided for said downwardly directed branch and the gas flowing through said upwardly directed branch to said inlet provided for said upwardly directed branch. The sample solution is caused to flow on the inner surface of the conduit deoxygenation section.

In the form of the invention in which a DME is used, the measurement of the current flowing between the DME and the working electrode is preferably synchronized with the detachment of the mercury drop from the mercury capillary at the end of which it is formed.

Correspondingly, the invention provides a method of voltammetric analysis, comprising the steps of comprising the steps of providing a voltammetric cell having, in addition to a reference electrode, a working electrode and a counter-electrode located below said working electrode;

causing the sample solution to flow in a thin layer in contact and equicurrent with a stream of an inert gas, whereby to remove oxygen therefrom;

separating the solution stream from the gas stream; feeding the solution stream to a space between said working electrode and said counter-electrode;

drawing said solution stream from a point above said space;

applying a potential between said working electrode and said reference electrode; and monitoring the current flowing between said working electrode and said counter electrode.

Preferably, the working electrode is a DME.

When the working electrode is a DME the method further comprises, in an embodiment of the invention, synchronizing the monitoring of the current flowing between the DME and the counter-electrode with the fall of the mercury drops of said DME, whereby to monitor said current when said mercury drops have a given, reproducible volume.

DETAILED DESCRIPTION OF THE PREFERRED EMBODIMENTS

The embodiment illustrated comprises a dropping mercury electrode, but, as stated hereinbefore, the invention can be carried out with other types of electrodes, such as gold, platinum, glassy carbon electrodes and the like.

Figure 1:
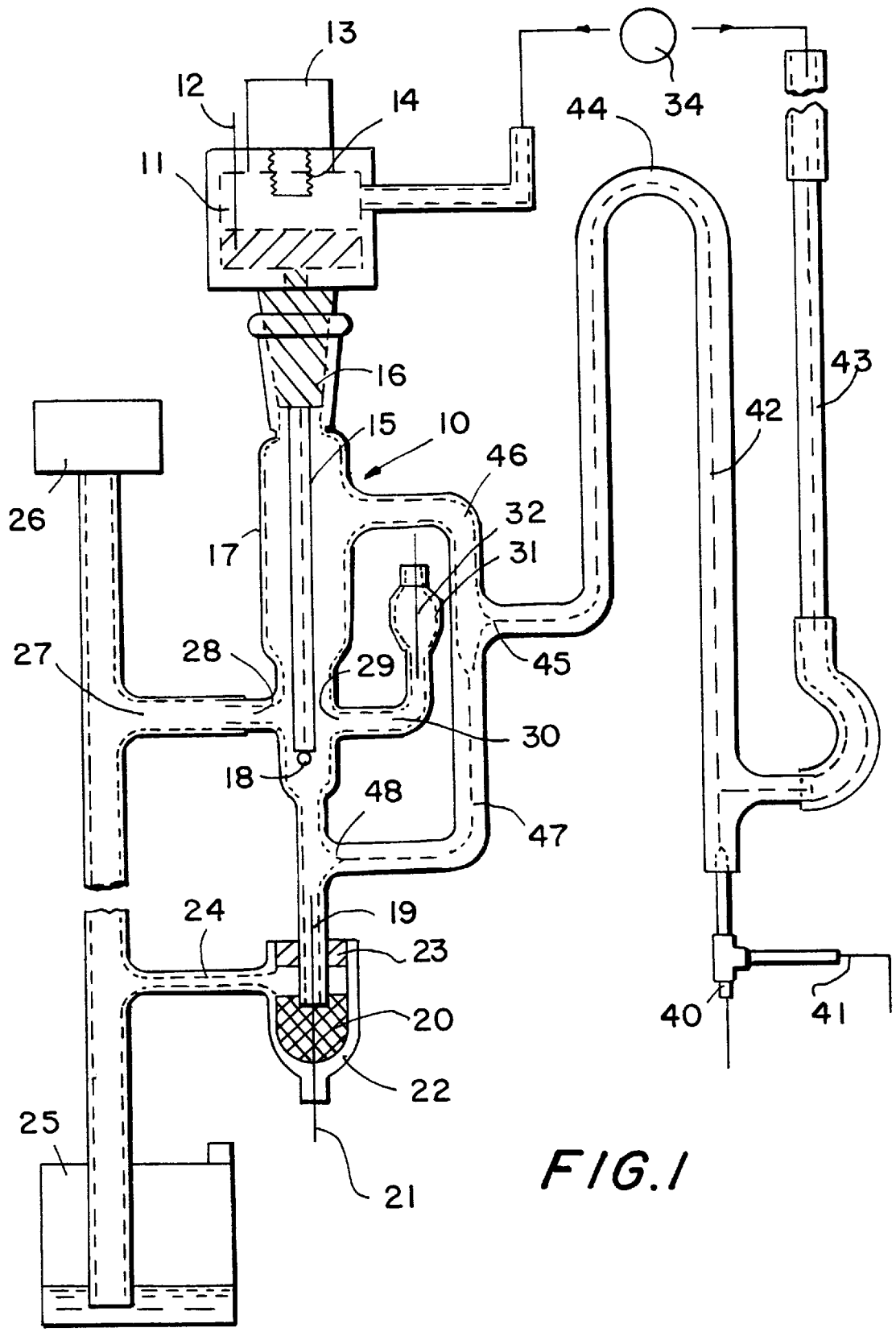
FIG. 1 is a schematic representation of a voltammetric cell according to an embodiment of the invention, seen in vertical cross-section.

With reference now to FIG. 1, the electroanalytical apparatus according to the invention comprises a cell proper that is generally indicated at 10 and which comprises, starting at the top, a mercury reservoir 11. Numeral 12 indicates a platinum wire used as an electrical contact, and numeral 13 indicates a refill stopper having a screw 14. From reservoir 11, mercury falls to capillary 15 which passes through a stopper 16 of a suitable elastic matter, preferably Teflon, which closes the top of the cell body, generally indicated at 17, said cell body being preferably made of glass or teflon. Capillary 15 has an inner diameter from 0.07 to 0.1 and preferably about 0.08 mm. The working electrode is a mercury drop 18 is formed at the end of capillary 15. Below the zone at which that drop is formed, the cell body 17 forms a pipe portion 19, which is full of sample solution. The sample solution is retained at the end of said pipe portion, because this latter sinks into a standing mercury mass 20. Said mercury mass, together with platinum wire 21, one end of which is immersed therein, constitutes the counter-electrode, and is contained in a reservoir 22, which is provided at its top with a stopper 23 through which pipe 19 passes. The reservoir 22 is connected with an outlet pipe 24. The mercury contained in the drops, which fall through pipe section 19 to reservoir 22, are added to mass 20. Concurrently, mercury overflows from reservoir 22 and is discharged through outlet 24 to sump 25.

The cell body 17 is provided with an exit 29, which is closed by a porous ceramic body 30 and leads to an auxiliary vessel 31, filled with a potassium chloride solution and containing the reference electrode 32.

The porous ceramic body 30 electrically connects the cell to the reference electrode by ion mobility,.

A source of nitrogen, or other inert gas, such as helium, such as a pressure tank, not shown, is provided, as schematically indicated at 34.

The sample solution to be analyzed and which contains the electrolyte, is fed to the apparatus through inlets 40 and 41. It can be drawn into the inlets by the vacuum applied to the cell, or by a peristaltic pump which feeds it to said inlets, or both. In FIG. 1, a vacuum pump, not illustrated but schematically indicated at 26, creates a vacuum in the cell through an exit pipe 27, which is connected to exit 28 formed in the body 17 of the cell. The vacuum in the cell applies suction to the inlet, drawing the sample solution into the said inlets. Through the said inlets, the solution is led into the deoxygenation means. In the embodiment illustrated, this means is constituted by a conduit, indicated in this embodiment as pipe 42, but different deoxygenation means, such as spray columns or the like, could be employed. If different deoxygenation means, such as a spray is employed, the directions of flow of the sample solution and of the inert gas will be adapted to the structure of said means, in a way that will be obvious in each case to persons skilled in the art, and may be different from those obtaining in this embodiment. Nitrogen is fed to the same conduit through pipe 43. The pressure of the nitrogen prevents the solution from rising into pipe 43. Thus, the sample solution flows in a thin layer on the inner surface of pipe 42, while nitrogen flows centrally of said pipe; and oxygen is removed from the solution and becomes mixed with the nitrogen. Pipe 42 reaches its highest point, 44, and then continues downwardly to an outlet 45 where it branches out into an upper or gas branch 46 and a lower or liquid branch 47. At the outlet 45, the sample solution becomes separated from the nitrogen stream. This latter flows upwardly through branch 46, while the sample solution flows downwardly through branch 47. The nitrogen flows into the body 17 of the cell, around mercury capillary 15, and out of it through exit 28 and pipe 27, to vacuum pump 26. The sample solution enters the cell body 17 at the inlet 48, situated between the mercury drop 18 and the pipe section 19. It is trapped in said pipe section by the mercury mass 20 and fills it completely, covering platinum electrode 21 and completely filling the space between the mercury mass 20 and the mercury drop 18. It then flows upwards over the mercury capillary 15 and finally out of the cell body 17 through outlet 28 and pipe 27, fling therefrom into sump 25. As set forth hereinbefore, sump 25, in this embodiment, also receives the mercury overflow; however, separate sumps could be provided for the solution and the mercury by means of a phase separator.

Means, not shown and conventional, are provided for applying a potential between the mercury drop 18 and the reference electrode 31.

Figure 2:
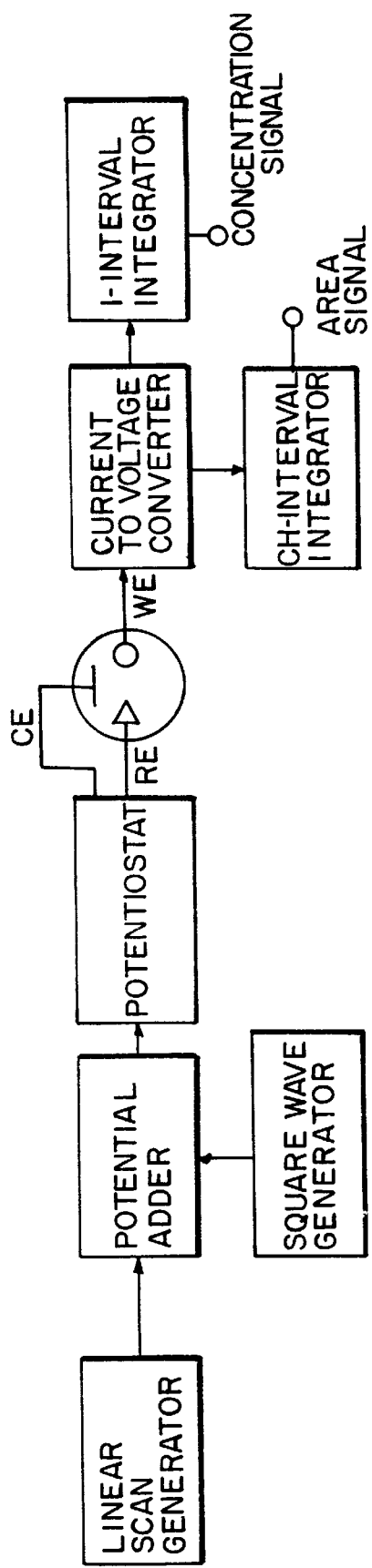
FIG. 2 is a block diagram illustrating the operation of the circuit employed for controlling the fall of the mercury drop, in an embodiment of the invention.
Figure 2:
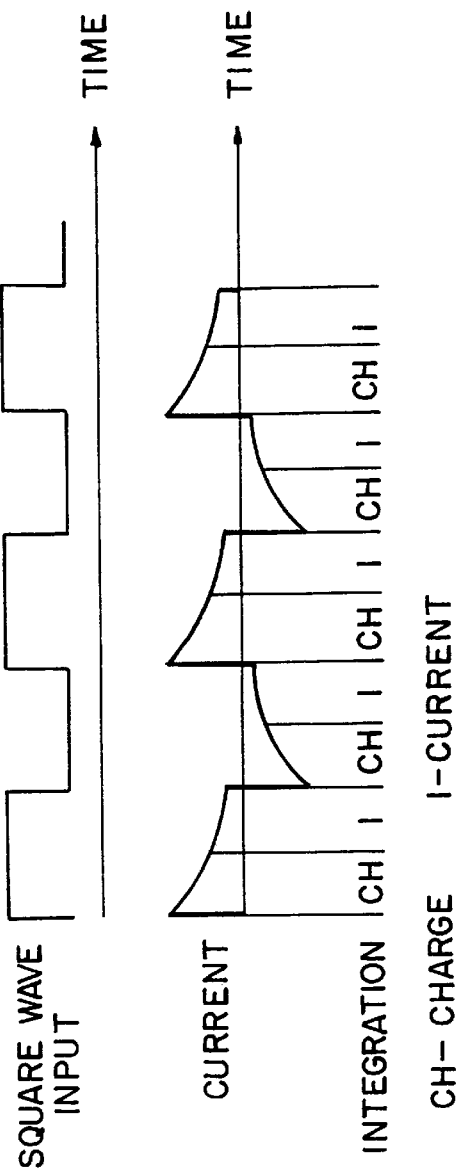

FIG. 2 is a block diagram illustrating the operative connection between the several electrodes. WE, RE and CE indicate the working electrode, the reference electrode and the counter-electrode respectively. The square wave produces a periodic current between the working and the counter-electrodes. In the first half of each half-period of the square wave the working electrode is loaded with a charge that depends on the new potential. The charge is proportional to the area of the mercury drop. When the mercury drop falls, the area is close to zero and the charge is zeroed. Therefore the said first half serves to reveal the fall of the drop. A current, due to the reduction or oxidation of the ions in the solution, is generated at the moment that the square wave changes its polarity. It is measured only in the second half of the cycle half-period, because in the first half the strong loading current masks the reduction or oxidation current.

Examples of measurements illustrating the operation of the cell according to the invention will now be described.

EXAMPLE 1

Determination of the Concentration of Lead in a Solution

First stage

A sample solution, together with a supporting electrolyte Buffer Ammonia 0.1M, was introduced into a cell according to the embodiment described.

The electrical scanning was carried out as follows:

| amplitude of the square wave | 50 mV |
|---|---|
| frequency | 25 Hz |
| scanning speed | 0.1 V/S |

Figure 3:
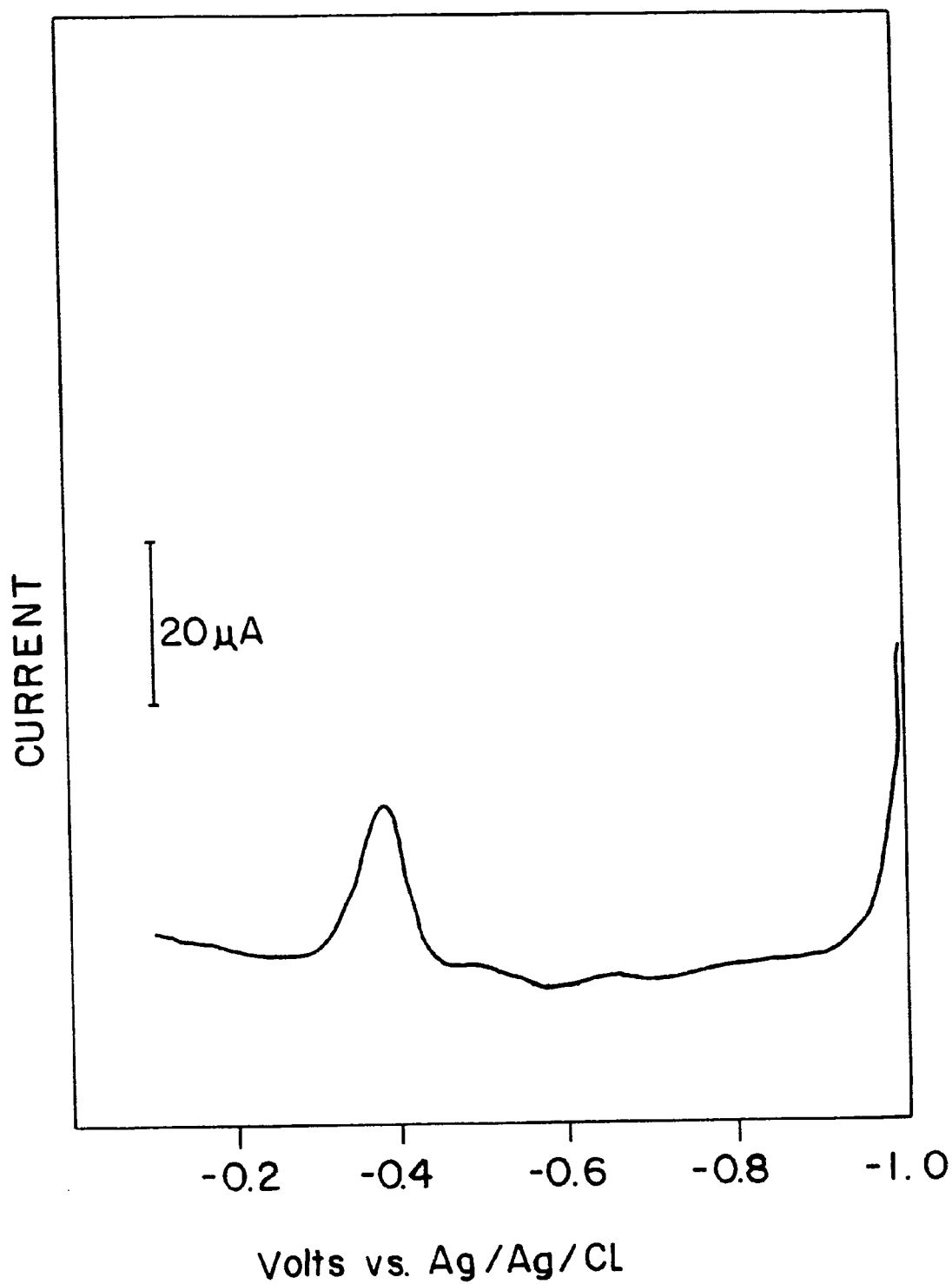
FIGS. 3 to 5 are diagrams illustrating examples of the invention.

The results are shown in FIG. 3. The position of the peak is characteristic of the component the concentration of which is to be determined, while its area is proportional to the component concentration.

Second stage

The same operations as in the first stage were carried out under the same conditions, but with a sample solution containing 1 ppm of standard lead. The results are shown in FIG. 4.

Figure 4:
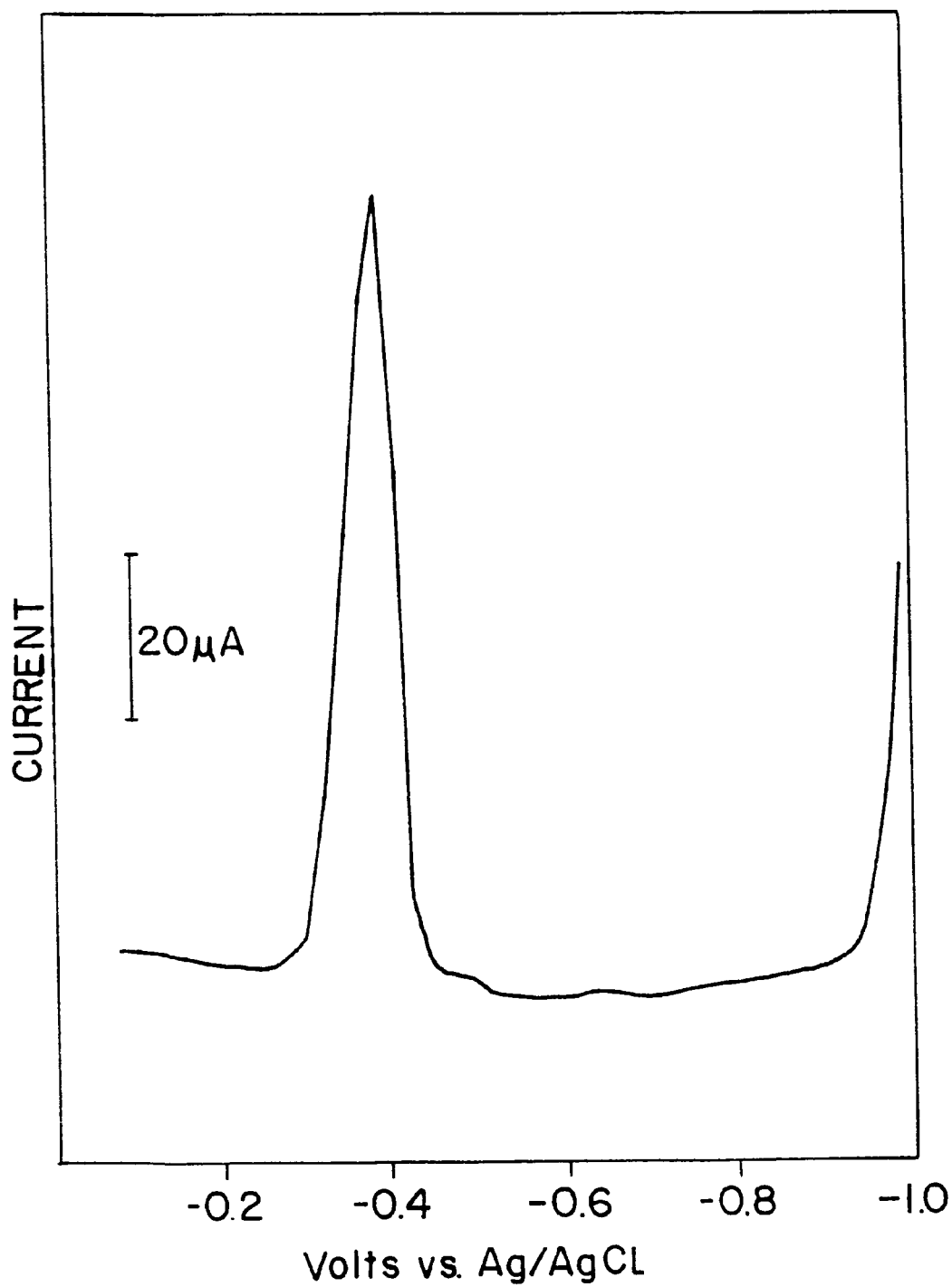

From the ratio of the area of the peak of FIG. 3 to that of FIG. 4 the lead concentration in the sample solution was calculated to be 0.23 ppm.

EXAMPLE 2

Speed and Sensitivity of the Cell Under In-Flow Conditions

As hereinbefore mentioned, it is very important for in-flow operation that the cell have short reaction time and reveal the any changes in the concentration of metal ions in the sample solution shortly, e.g. a few seconds, after they have occurred. Such short reaction times are not possessed by prior art cells. The following example shows that the cell according to the invention reacts very quickly to metal ion concentration changes and constitutes a considerable improvement over the prior art in this respect as well A solution containing 100 ppb of cadmium ions ($Cd^{+2}$) together with an electrolyte containing Buffer acetate 1.0M was caused to flow through a cell according to the embodiment described. The electrical scanning conditions were the same as in Example 1 and the frequency of the potential scanning was one scan every 6 seconds.

Figure 5:
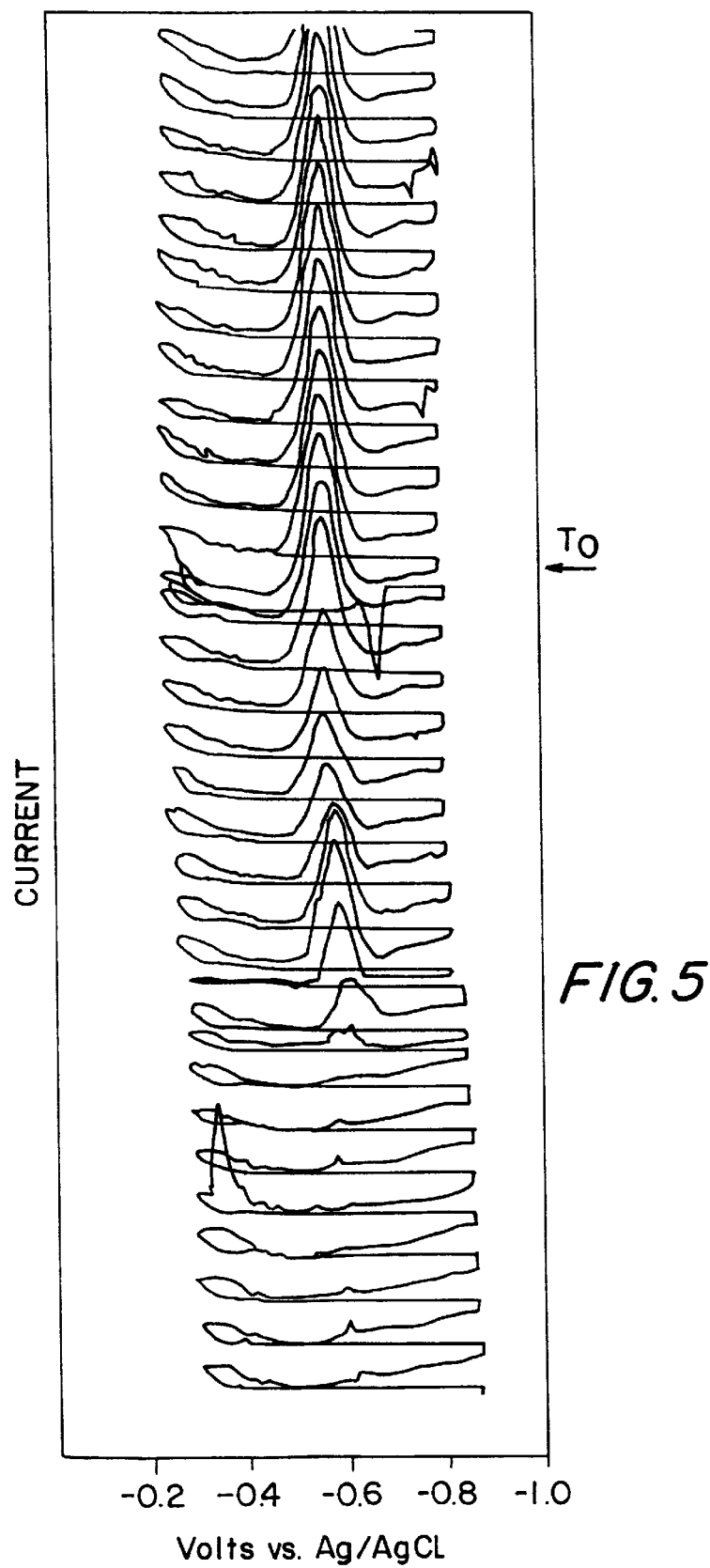

FIG. 5 illustrates the results of the potential scanning, starting from the top. At the point marked To, the cadmium solution was substituted with pure water containing acetate buffer, so that henceforth the cell contained the electrolyte solution with buffer and no cadmium. The cadmium peak disappeared at one minute from To.

The above example proves the high reaction speed of the cell when a metal ion, that was present, disappears from the sample solution. Obviously, the cell would behave in the same way if a metal ion, that was absent, should appear in said solution.

While an embodiment of the invention has been described by way of illustration, it will be apparent that the invention may be carried out by persons skilled in the art with many variations, modifications and adaptations, without departing from its spirit or exceeding the scope of the claims.

I claim:

1. An electroanalytical cell comprising:
   a) a cell body housing, a reference electrode, a working electrode and a counter-electrode disposed at the lowermost portion of the working electrode;

b) deoxygenation means for removing oxygen from a sample solution;

c) means for feeding the sample solution to the deoxygenation means, means for feeding an inert gas stream to the deoxygenation means and means for causing the sample solution to flow as a stream in contact and equicurrent with the inert gas stream in the deoxygenation means;

d) means for separating the sample solution from the inert gas stream and for removing the inert gas from the deoxygenation means after deoxygenation of the sample solution;

e) an inlet for the deoxygenated sample solution provided in the cell body housing disposed in a space between the working electrode and the counter-electrode;

f) an exit for the deoxygenated sample solution provided in the cell body housing disposed above the working electrode; and g) vacuum and or pressure means for causing the deoxygenated sample solution to flow to said exit and to be discharged therefrom, such that the space between the working electrode and the counter-electrode is constantly filled with the deoxygenated sample solution.

2. A cell according to claim 1, wherein the working electrode is chosen from the group consisting of a mercury, gold, platinum and glassy carbon electrode.

3. A cell according to claim 1, wherein the working electrode is a dropping mercury electrode (DME), comprising a mercury capillary fed with mercury from a mercury reservoir, whereby a mercury drop is periodically formed and separated from the lowermost end of said capillary.

4. A cell according to claim 3, wherein the counter-electrode comprises a stationary mass of mercury, positioned to receive the mercury drops of the DME.

5. A cell according to claim 4, comprising a vessel for retaining the stationary mercury mass, a sump, and an exit conduit from said vessel to said sump, to permit overflow of mercury to said sump.

6. A cell according to claim 3, wherein the counter-electrode comprises a stationary mass of mercury, positioned to receive the mercury drops of the DME.

7. A cell according to claim 3, wherein the DME comprises a mercury capillary having an inner diameter between 0.07 and 0.1 mm.

8. A cell according to claim 1, wherein the deoxygenation means comprises a deoxygenation conduit and means for feeding thereto the sample solution and an inert gas, said conduit comprising a deoxygenation section wherein the solution and the gas flow together in equicurrent and branching out at the end of said deoxygenation section into an upwardly directed branch and a downwardly directed branch, an inlet being provided for said downwardly directed branch in said cell body in the space between said electrode and said working electrode and an inlet being provided for said upwardly directed branch in said cell body above said electrode, the sample solution flowing through said downwardly directed branch to said inlet provided for said downwardly directed branch and the gas flowing through said upwardly directed branch to said inlet provided for said upwardly directed branch.

9. A cell according to claim 8, wherein the sample solution is caused to flow on the inner surface of the conduit deoxygenation section.

10. A cell according to claim 1, wherein the inert gas is selected from the group consisting of nitrogen and helium.

11. A cell according to claim 1, wherein the cell body is provided with a branch housing the reference electrode, located below the level of the sample solution.

12. A cell according to claim 1, further comprising an inlet for an upwardly directed branch into the cell body above the exit.

13. A cell according to claim 1, further comprising means for synchronizing the measurement of the current flowing between the DME and the counter-electrode with the detachment of the mercury drop from the mercury capillary.

14. A method of voltammetric analysis, comprising the steps of providing a voltammetric cell having, in addition to a reference electrode, a working electrode and a counter-electrode located below said working electrode;

causing a sample solution to flow as a stream in a thin layer in contact and equicurrent with a stream of an inert gas, in order to remove oxygen from the sample solution stream;

separating the solution stream from the gas stream;

feeding the solution stream to a space between said working electrode and said counter-electrode;

drawing said solution stream from a point above said space;

applying a potential between said working electrode and said reference electrode; and monitoring the current flowing between said working electrode and said counter-electrode.

15. A method according to claim 14, wherein the working electrode is a dropping mercury electrode (DME).

16. A method according to claim 15, further comprising synchronizing the monitoring of the current flowing between the DME and the counter-electrode with the fall of the mercury drops of said dropping mercury electrode, whereby to monitor said current when said mercury drops have a given, reproducible area.

17. A method according to claim 16, wherein the synchronization of the monitoring of the current flowing between the mercury drop electrode and the counter-electrode with the fall of the mercury drops of said mercury drop electrode is effected by applying between said electrodes a square wave potential, whereby a periodic current between said working electrode and said counter-electrode is produced and the working electrode is loaded with a charge, determining the fall of the drop from the zeroing of said charge, and measuring the reduction-oxidation current from the moment in which said square wave changes its polarity.

* * * * *